(12) United States Patent
Campbell

(10) Patent No.: US 6,575,741 B2
(45) Date of Patent: *Jun. 10, 2003

(54) ORAL ANCHORAGE

(75) Inventor: Duncan Fraser Campbell, Argyll & Bute (GB)

(73) Assignee: Zygomatics Limited, Argyll & Bute (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,506

(22) PCT Filed: May 11, 1998

(86) PCT No.: PCT/GB98/01342

§ 371 (c)(1),
(2), (4) Date: Dec. 1, 1999

(87) PCT Pub. No.: WO98/51242

PCT Pub. Date: Nov. 19, 1998

(65) Prior Publication Data

US 2002/0068254 A1 Jun. 6, 2002

(30) Foreign Application Priority Data

May 9, 1997 (GB) ............................................. 9709298

(51) Int. Cl.⁷ ................................................. A61C 3/00
(52) U.S. Cl. ........................... 433/18; 606/74; 24/16 PB
(58) Field of Search ............................ 433/18, 23, 19; 606/74; 24/16 PB (56) References Cited

U.S. PATENT DOCUMENTS

| | | | |
|---|---|---|---|
| 2,035,135 A | 3/1936 | Lebow | |
| 2,086,656 A | 7/1937 | Woodward | |
| 2,481,177 A | 9/1949 | Tofflemire | |
| 3,452,436 A * | 7/1969 | De Woskin | 433/23 |
| 3,570,497 A * | 3/1971 | Lemole | 606/74 |
| 4,119,091 A * | 10/1978 | Partridge | 606/74 |
| 4,167,813 A | 9/1979 | Forster | |
| 4,198,753 A * | 4/1980 | Förster | 433/23 |
| 4,813,416 A * | 3/1989 | Pollak et al. | 606/74 |
| 4,813,869 A | 3/1989 | Gatewood | |
| 5,697,783 A * | 12/1997 | Wilson et al. | 433/23 |
| 6,050,998 A * | 4/2000 | Fletcher | 606/74 |

FOREIGN PATENT DOCUMENTS

| | | | |
|---|---|---|---|
| SU | 11191070 | * 11/1985 | 433/18 |
| WO | WO 88/06022 | * 8/1988 | 606/74 |
| WO | 98/28112 | 9/1996 | |

OTHER PUBLICATIONS

Wilson et al., "Subjective effects of double gloves on surgical performance", Surg. Eng., 1996, vol. 78, pp. 20–22.

(List continued on next page.)

Primary Examiner—Ralph A. Lewis
(74) Attorney, Agent, or Firm—Drinker Biddle & Reath LLP (57) ABSTRACT

The present invention provides an intra-oral anchorage which comprises a flexible belt that extends around and between the teeth of a patient. The belt has locking means fixed thereon to receive a free end portion of the belt and lock said portion against retraction therefrom. The locking means is in the form of a buckle. The intra-oral anchorage of the present invention can be used to hold a jaw in a fixed position, in the case of a broken jaw for example. It offers ease of application and therefore a reduction in the cost of surgery as well as eliminating the risk of "needle stick" injury inherent with cutting and bending multiple ends of wire. It causes less gum damage in placement and removal, which is similarly easier, faster and less uncomfortable for the patient.

17 Claims, 8 Drawing Sheets

OTHER PUBLICATIONS

Dauleh et al., "Needle prick injury to the surgeon—do we need sharp needles?", Surg. Edinb., Oct. 1994, vol. 39, pp. 310–311.

Jeffries, "Viral hazards to and from health care workers", Journal of Hospital Infection, 1995, vol. 30, pp. 140–155.

Carlton et al., "Percutaneous Injuries During Oral and Maxillofacial Surgery Procedures", Oral Maxillofac. Surg., 1997, vol. 55, pp. 553–556.

* cited by examiner

ORAL ANCHORAGE

FIELD OF THE INVENTION

This invention relates to a novel form of intra-oral anchorage, for use in oral surgical procedures.

BACKGROUND OF THE INVENTION

Intra-oral anchorage refers to a stable point within the mouth, usually a tooth, such that traction may be applied to a less fixed or a moveable structure. Alternatively, two or more anchorage points may be used so that teeth may be held firmly together such that a fracture site nay be aligned and/or that some other surgical procedure may be performed which would necessitate the occlusion being consistent throughout and after the procedure.

Figure 1A:
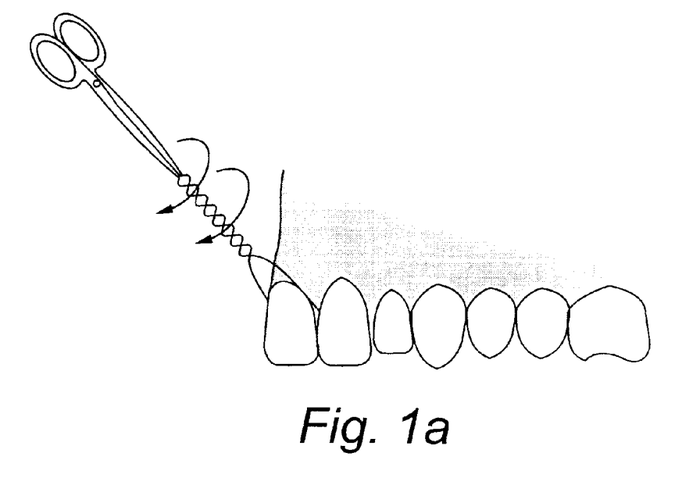
FIG. 1A: Illustrates the prior art method of intra-oral wiring.

This intra-oral anchorage is usually achieved by use of metal wires twisted tightly around the teeth (see FIG. 1A). Additionally, metal bars (arch bars) may be used to create multiple hooks as easy anchorage for traction or fixation (see FIGS. 1B and 1C). Once an anchorage point has been established, traction is usually achieved by means of elastic bands while fixation is by use of more metal wires.

This system of wiring is time consuming and requires skill, dexterity and training. It is so uncomfortable for the patient that it is almost invariably done during a general anaesthesia. The removal of the wire several weeks later is usually under local anaesthesia and is generally distressing and destructive of delicate gingival (gum) structures.

As result of the wire cutting, there are many sharp ends of wire which present hazards to the patient, operator and his assistant, as gloves and skin are often punctured by the wire. This results in a risk of transmission of blood borne infections particularly hepatitis and the AIDS virus which is a well known risk associated with current techniques.

Additionally, wire work hardens and fractures in placement and often stretches with functional load requiring readjustment.

SUMMARY OF THE INVENTION

Accordingly, the present invention provides anchorage for use in the treatment of oral fractures comprising a flexible belt of a dimension to extend around and between the teeth of a patient, the belt having locking means fixed thereon to receive a free end portion of the belt and lock said portion against retraction therefrom.

Preferably, the lock means is attached at one end to the belt, and may be generally in the form of a buckle.

Preferably, the locking means is in the form of a head having an aperture therethrough for receiving the end portion of the belt.

Preferably also the head has a one-way lock mechanism to allow advancement, but resist retraction of the belt in the aperture.

The belt may comprise two sections, a first section including the free end of the belt and typically being curved; and a second section between the first section and the locking means.

The second section is preferably profiled to co-operate and lockingly engage with the locking head.

Preferably, the first section has a smooth surface to facilitate passing the belt through inter-dental spaces.

The locking head may have on its outer face means for retaining a fixing member, for example an elastic band, a plastic tie, a wire or a bar, for inter-connecting and fixing to other locking heads.

Advantageously, there are no sharp edges on the anchorage which may be hazardous to the patient or the operator.

The locking means may comprise a plurality of inclined teeth on both the second section of the belt and an inner face of the locking head whereby the teeth co-operate such that the belt can only pass through the aperture in one direction.

The locking means may include an external plate to ensure a coherent fitting of the anchorage to a tooth; the plate may be concave, although it can be varied to suit any given tooth.

In use, where more than one anchorage is used, traction may be applied between the anchorages by wrapping elastic bands or other suitable means around retaining means such that the teeth or fracture points may be drawn into proper alignment and held in place.

The belt is typically between 10 and 14 centimeters in length and around 0.6 to 1.0 millimeters in width.

Said first section of the belt may be typically 1.5 to 3 centimeters long.

The locking head is preferably approximately 7 to 11 millimeters long and approximately 3 to 5 millimeters in width.

Further according to the invention there is provided a method of treating facial or law fractures or facilitating facial or jaw bone surgery, comprising extending a flexible belt around one or more of a patient's teeth, passing one end portion of the belt through locking means carried on the belt and tensioning the belt around the teeth by drawing it through the locking means, said locking means preventing retraction of the belt therefrom.

The belt is preferably of plastics material.

More preferably the belt is of Nylon having a tensile yield strength of between 50 to 80 $MN/m^2$ and a Rockwell hardness of between 100–140.

Optionally the belt, is of polyketone, having a tensile yield strength of between 50 to 80 $MN/m^2$ and a Rockwell hardness of between 100–140.

Optionally a portion of the belt, especially the first section of the belt may be of steel, having a tensile yield strength of between 175 to 2000 $MN/m^2$ and a modulus of elasticity of between 175 to 230 $GN/m^2$.

The plastic 'buckle' preferably faces outwards from the face of the tooth and incorporates a hook and location point for an arch bar. The entire device can be produced with no sharp edges and may have minor modifications of shape to facilitate placement.

BRIEF DESCRIPTION OF THE DRAWINGS

Embodiments of the invention will now be described by way of example with reference to the accompanying drawings in which:

DETAILED DESCRIPTION OF THE INVENTION

Figure 1B:
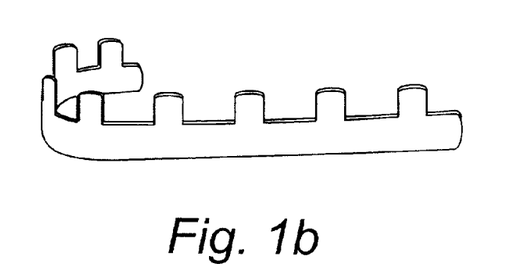
FIG. 1B: Illustrates an arch bar of the prior art.
Figure 1C:
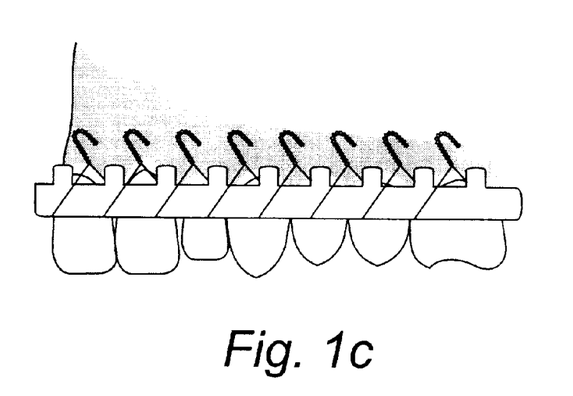
FIG. 1C: Illustrates an arch bar of the prior art anchored by intra-oral wiring.
Figure 2A:
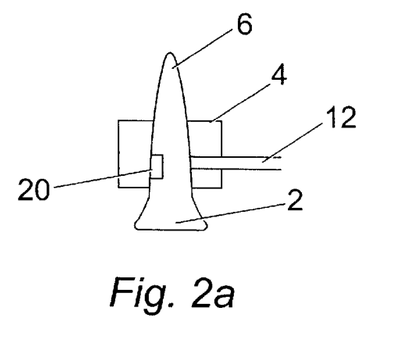
FIG. 2A: Illustrates an anterior view of the first embodiment of the anchorage.
Figure 2B:
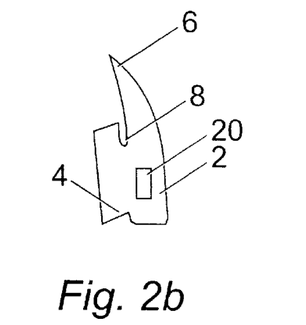
FIG. 2B: Illustrates the first embodiment of the anchorage viewed from the right hand side.
Figure 2C:
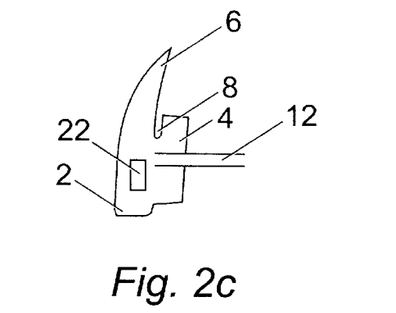
FIG. 2C: Illustrates the first embodiment of the anchorage viewed from the left hand side.
Figure 2D:
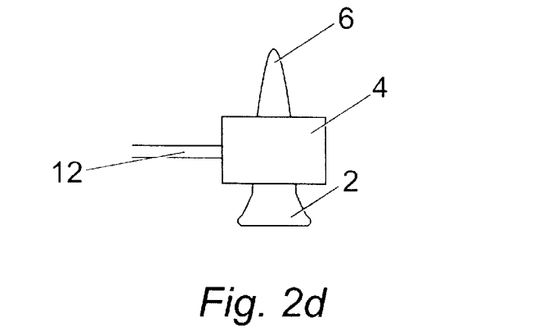
FIG. 2D: Illustrates the posterior view of the first embodiment of the anchorage.
Figure 3A:
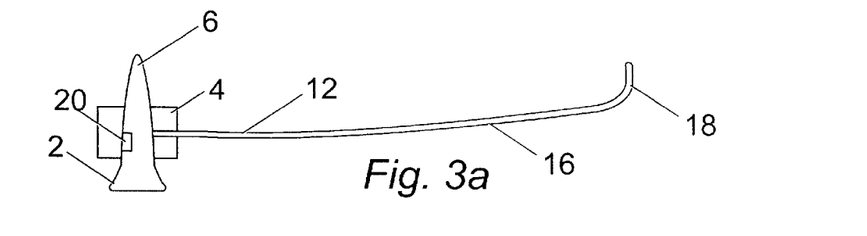
FIG. 3A: Shows the first embodiment of the anchorage 'open'.
Figures 3B, 3C:
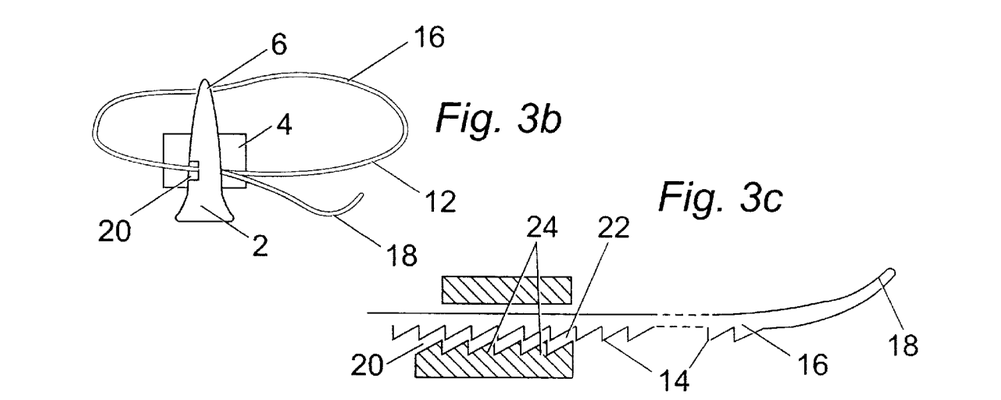
FIG. 3B: Shows the first embodiment of the anchorage 'closed'.
FIG. 3C: Shows the locking mechanism.
Figure 4A:
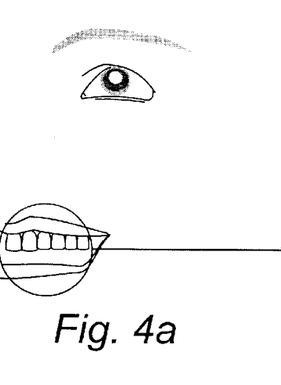
FIGS. 4A–D: Illustrates the device being fitted to a tooth.
Figure 4B:
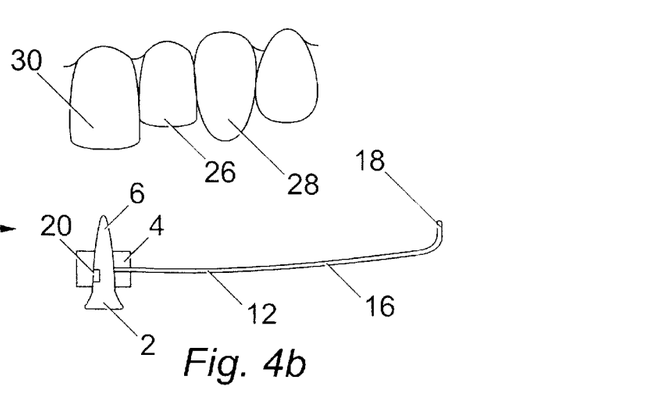
Figure 4C:
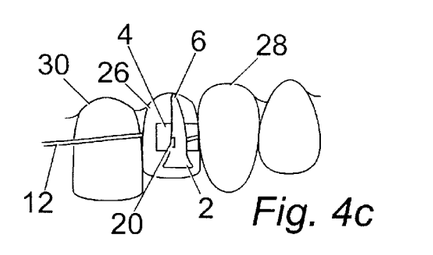
Figure 4D:
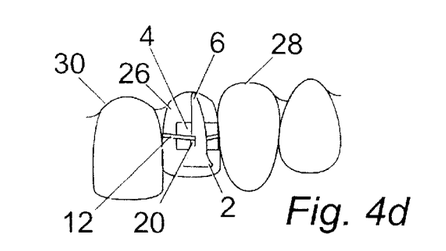
Figure 5:
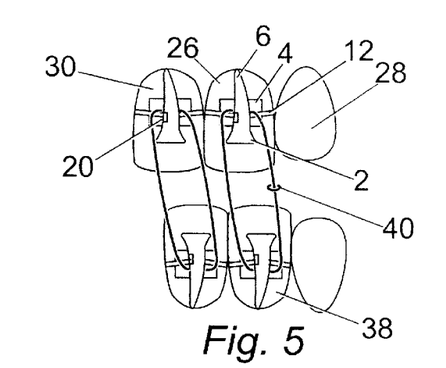
FIG. 5: Shows traction being applied using elastic bands wrapped around the hooks.

FIGS. 1A–1C shows the prior use method of wiring an arch bar to teeth to provide a plurality of anchor points for traction to be applied.

The oral anchorage of the first embodiment of the invention is formed from a single piece of plastics material 2. The plastics material 2 is shaped to form a flat section 4 and a hook 6, which adjoins flat section 4. Between the flat section 4 and hook 6 there is a groove 8 for placement of arch bar 10. Hook 6 has a belt 12 which runs perpendicular from hook 6. Belt 12 may have teeth 14 on its upper and or side sections and is in sections 16 and 18; section 16 is linear and section 18 is curved. Hook 6 also has apertures 20 and 22 for entry and exit access for belt 12, and has teeth 24 between apertures 20 and 22, which cooperate with the teeth of belt 12, to produce a one-way locking mechanism. Aperture 20 is funnelled for ease of belt entry.

In use the first embodiment of the oral anchorage of the invention is offered to outside face of tooth 26. Belt 12 is pushed through the gap between teeth 26 and 28, passed around the back of tooth 26 and through the gap between teeth 26 and 30. Belt 12 is then threaded into aperture 20, pulled through aperture 22 and pulled tight until taut around tooth 26. Belt 12 is held in position by virtue of the cooperation of its teeth 14 with teeth 24. The locking mechanism is of a one-way type such that once the belt 12 is passed through the apertures 20 and 22 it cannot be drawn back in the opposite direction. Any excess belt 12 which is left protruding from aperture 22 is cut away using any conventional technique.

Figure 13A:
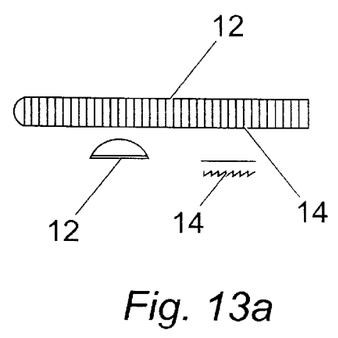
FIG. 13A: Illustrates the belt of the anchorage with teeth on its upper side viewed from the top, in cross section and from the side.
Figure 13B:
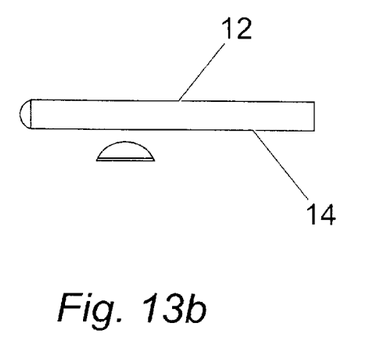
FIG. 13B: Illustrates the belt of the anchorage viewed from the top and in cross section.
Figure 13C:
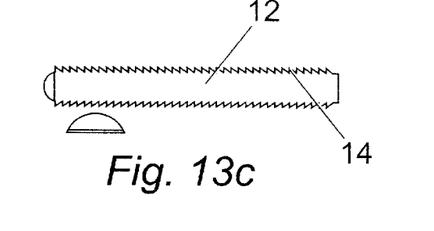
FIG. 13C: Illustrates the belt of the anchorage with teeth on its aide viewed from above and from the right hand side.
Figure 14A:
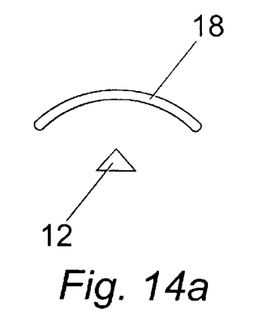
FIG. 14A: Illustrates the first section of the belt of the anchorage viewed from the side and in cross section.
Figure 14B:
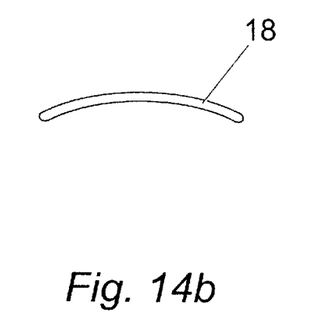
FIG. 14B: Illustrates the curvature of the first section of the belt of the anchorage viewed from the side.
Figure 15A:
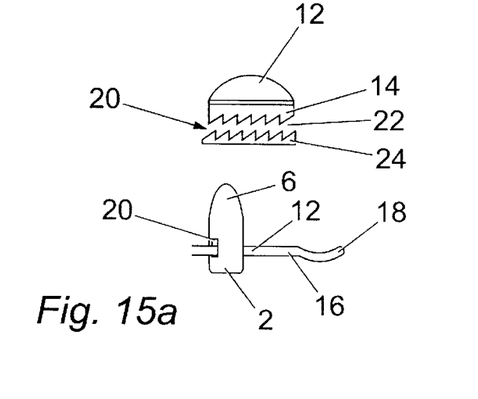
FIG. 15A: Illustrates how the teeth of the belt cooperate with the teeth of the anchorage.

The locking mechanism of the belt 12 between apertures 20 and 22 may vary. Teeth 14 on belt 12 may be on the longditudal side 32 or the vertical side 34 of belt 12.

Figure 15B:
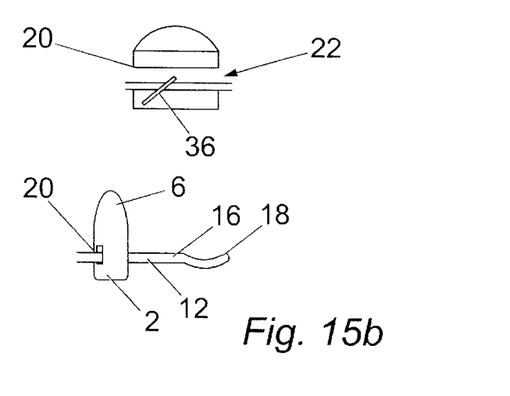
FIG. 15B: Illustrates the metal member locking system.

Alternatively a metal member 36, positioned between the apertures 20 and 22 within the anchorage 2, and angled so that the belt may pass one way over the metal member 36 may comprise the locking mechanism.

Once attached to tooth 26 the oral anchorage may cooperate with another oral anchorage, which has been similarly attached to tooth 38. By virtue of an elastic band, plastic ties or ligature wires 40 traction can be provided between the two oral anchorages, fixing jaw 42 in position for healing to occur.

Figure 6A:
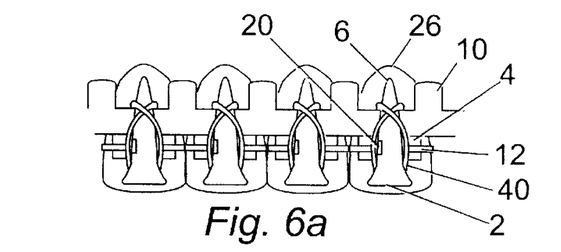
FIG. 6A: Shows an arch bar fitted in place.
Figure 6B:
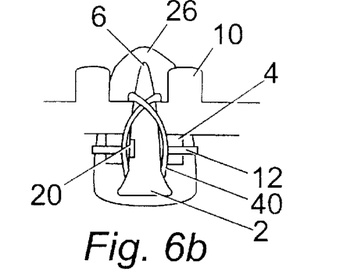
FIG. 6B: Shows an arch bar secured in place by an elastic band.

An arch bar 10 may be fixed into grooves 8 The arch bar is held in place by an elastic band 40 or by close adoptation to facets in the buckle.

The oral anchorage of the second embodiment of the invention is formed from a single piece of plastics material 2. The plastics material 2 is shaped to form a hook 6 having a groove 8 for placement of elastic band 40. Hook 6 has a belt 12 which runs perpendicular from hook 6. Belt 12 has teeth 14 and is in sections 16 and 18; section 16 is linear and section 18 is curved. Hook 6 also has apertures 20 and 22 for entry and exit access for belt 12 with teeth 24 between apertures 20 and 22, which cooperate with the teeth of belt 12 to produce a one-way locking mechanism.

Figure 15C:
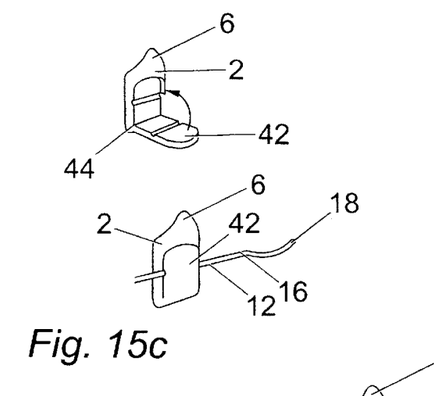
FIG. 15C: Illustrates the third embodiment of the anchorage with the flap open and also closed, viewed from the front.

The oral anchorage of the third embodiment of the invention is formed from a single piece of plastics material 2. The plastics material 2 is shaped to form a hook 6 for placement of elastic band 40 and has a flap 42 hinged about the anterior end 44 of anchorage 2. Hook 6 has a belt 12 which runs perpendicular from hook 6. In use the anchorage is applied to a tooth 24 as in the first embodiment. The difference from the first embodiment is that belt 12 is restrained in anchorage 2 by closing flap 42 tight against anchorage 2.

Figure 15D:
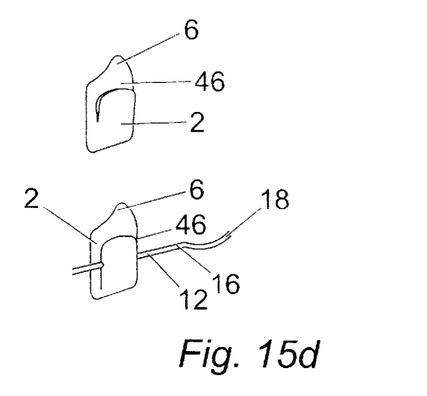
FIG. 15D: Illustrates the fourth embodiment of the anchorage and also when in use, viewed from the front.

The oral anchorage of the fourth embodiment of the invention is formed from a single piece of plastics material 2. The plastics material 2 is shaped to form a hook 6 for placement of elastic band 40 and has an incision 46 cut into the anchorage 2 toward its anterior end. Incision 46 is tapered from its point of incision. Hook 6 has a belt 12 which runs perpendicular from hook 6. In use the anchorage is applied to a tooth 24 as in the first embodiment. The difference from the first embodiment is that belt 12 is restrained in anchorage 2 pulling the belt right in incision 46.

Figure 15E:
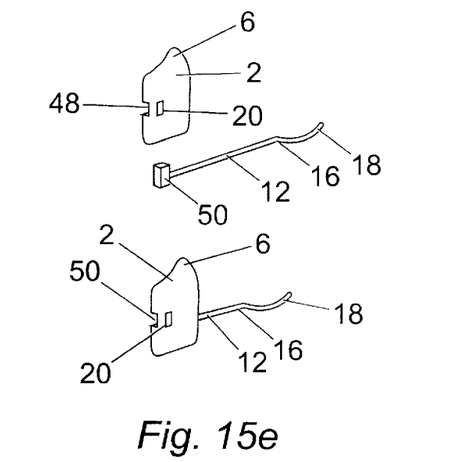
FIG. 15E: Illustrates the fifth embodiment of the anchorage and also when in use attached to a belt, viewed from the front.
Figures 16, 17A:
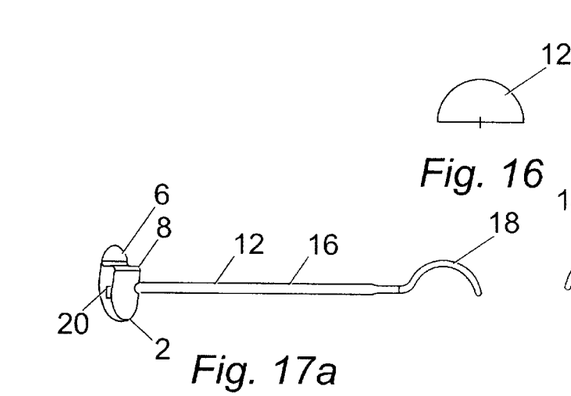
FIG. 16: Illustrates the belt of the anchorage viewed in cross section.
FIG. 17A: Illustrates a perspective view of the second embodiment of the anchorage.
Figure 17B:
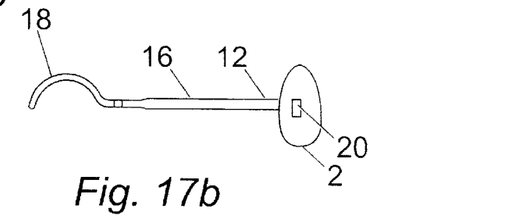
FIG. 17B: Illustrates the second embodiment of the anchorage viewed from the left hand side.
Figure 17C:
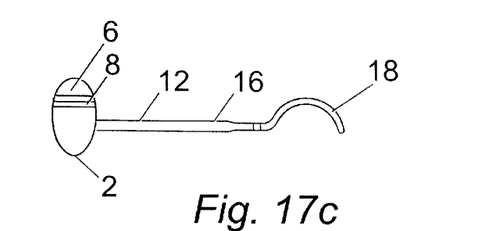
FIG. 17C: Illustrates the second embodiment of the anchorage viewed from the top side.
Figure 17D:
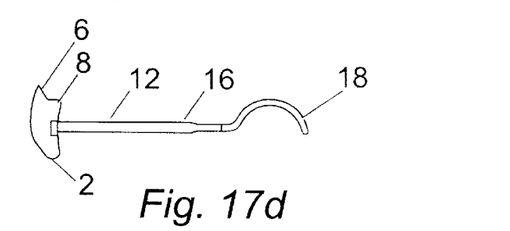
FIG. 17D: Illustrates the second embodiment of the anchorage viewed from the right hand side.
Figure 18A:
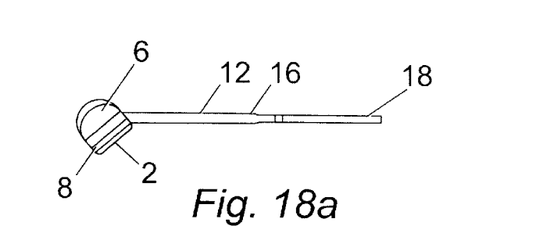
FIG. 18A: Illustrates the second embodiment of the anchorage viewed from above.
Figure 18B:
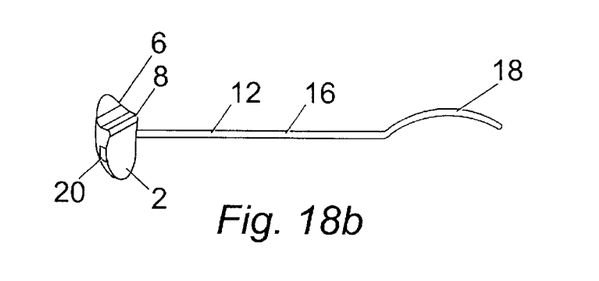
FIG. 18B: Illustrates the second embodiment of the anchorage viewed from the right hand side.

The oral anchorage of the fifth embodiment of the invention is formed from a single piece of plastics material 2. The plastics material 2 is shaped to form a hook 6 for placement of elastic band 40 and has an incision 48 cut into the side of anchorage 2. Incision 48 is designed to cooperate with a belt 12, which has a bulbous end 50, The bulbous end 50 is restrained in incision 48 as the belt is pulled tight in its attachment to a another oral anchorage.

Figure 7A:
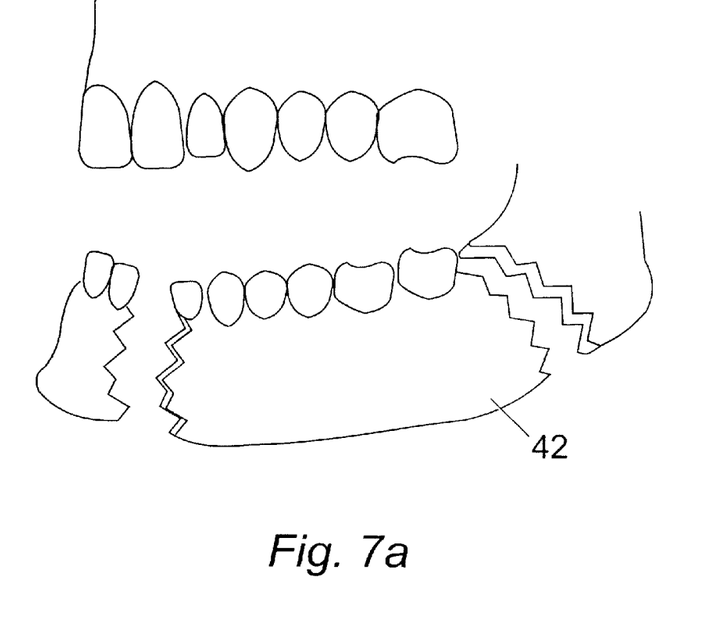
FIG. 7A: Shows a fracture at two positions.
Figure 7B:
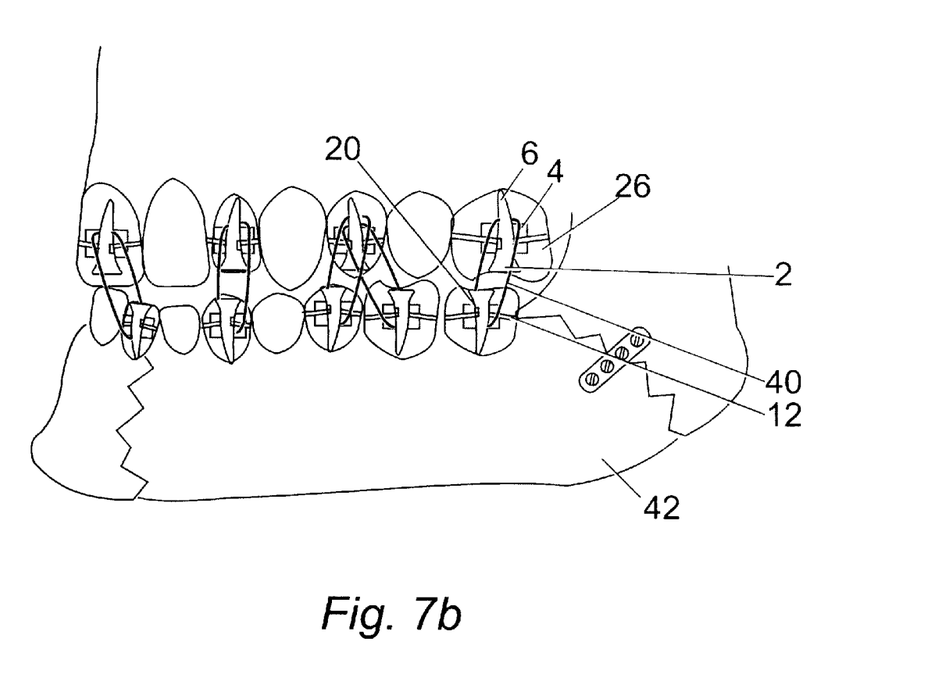
FIG. 7B: Shows the fracture sites realigned with a screw plate in place.
Figure 8A:
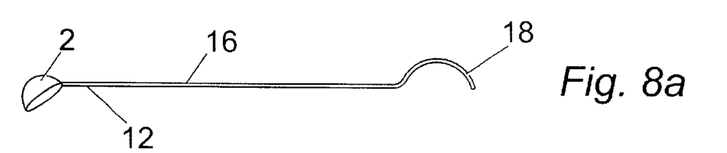
FIG. 8A: Illustrates a top view of the second embodiment of the anchorage.
Figure 8B:
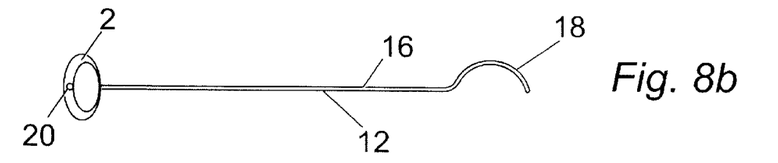
FIG. 8B: Illustrates the second embodiment of the anchorage viewed from the right hand side.
Figure 8C:
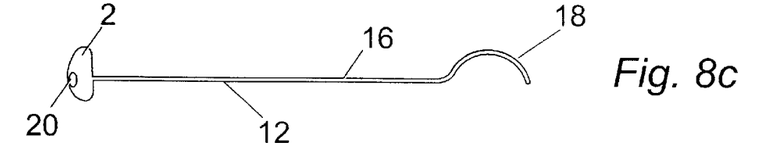
FIG. 8C: Illustrates the second embodiment of the anchorage viewed from the left hand side.
Figure 9:
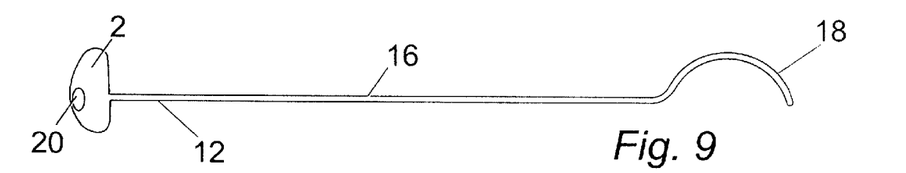
FIG. 9: Illustrates the second embodiment of the anchorage viewed from the left hand side.
Figure 10:
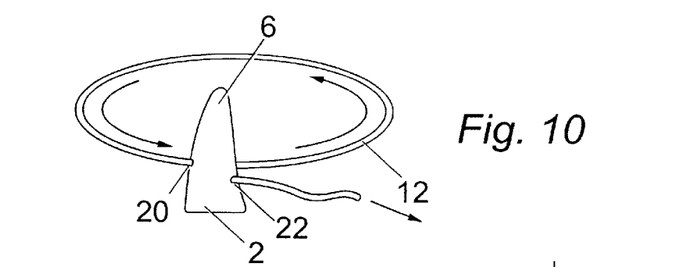
FIG. 10: Illustrates the pulling taut of the belt within the anchorage.
Figure 11A:
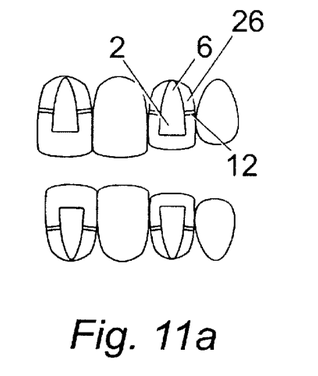
FIG. 11A: Illustrates anchorages attached to teeth viewed from the front.
Figure 11B:
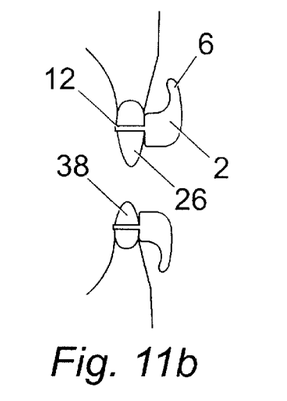
FIG. 11B: Illustrates anchorages attached to teeth viewed from the side.
Figure 11C:
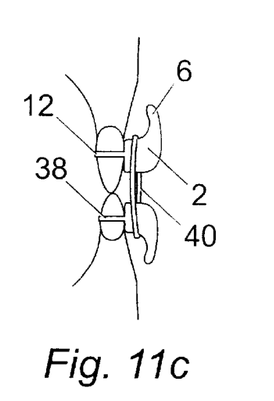
FIG. 11C: Illustrates anchorages attached to teeth with an elastic band placed over the hooks, viewed from the side.
Figure 12A:
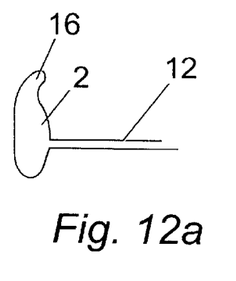
FIG. 12A: Illustrates the second embodiment of the anchorage viewed from the right hand side.
Figure 12B:
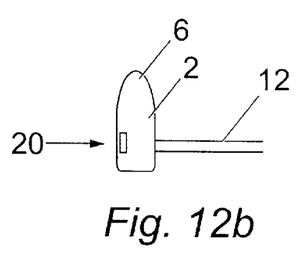
FIG. 12B: Illustrates the second embodiment of the anchorage viewed from the right hand side.
Figure 12C:
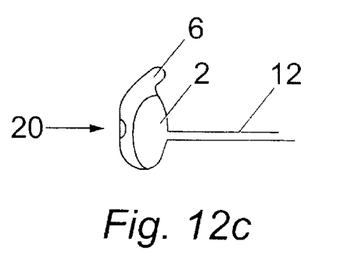
FIG. 12C: Illustrates the second embodiment of the anchorage viewed from the right hand side.

In the case of a fracture (see FIG. 7A), once the teeth are brought into their correct relationship, the fracture sites will necessarily be correctly aligned. Using the hooks as anchorage points, ligature wires, strong elastic bands, or plastic ties would hold this stable for weeks to allow healing or briefly to allow placement of a rigid metal plate, fixed by screws (see FIG. 7B).

The oral anchorage of embodiments of the present invention then provide anchorage points for the application of traction to teeth, particularly in the case of a broken jaw which is to be held in a fixed position. It offers a number of advantages over the conventional intra-oral anchorage method of metal wires as a result of its construction and ease of application. Particularly as there are no sharp ends of metal wires there is a much lower risk of "needle stick" injury to both patient and surgeon.

The present invention is easier to apply to a patient, resulting in lower operating time (and resultant lower costs) in applying and removing the anchorage and less damage to the delicate gum tissue in placement and removal. The anchorages are also sterile packed, are biologically inert and are compatible with other prosthetic and surgical technology/equipment.

REFERENCES

1. S. J. Wilson, A. Uy, D. Sellu and M. A. Jaffer, Ann. R. Coll. Surg. Engl., 1996, 78, 20–22.
2. M. I. Dauleh, A. D. Irving and N. H. Townell, J. R. Coll. Surg. Edinb., 1994, 39, 310–311.
3. D. J. Jeffries, J. Hospital Infection, 1995, 30, 140–155.
4. J. E. Carlton, T. B. Dodson, J. L. Cleveland, S. A. Lockwood, J. Oral. Maxillofac. Surg., 1997, 56, 553–556.

What is claimed is:

1. An anchorage for use in treatment of oral fractures comprising a flexible and wholly or substantially plastic belt of a dimension able to fit between the intra-dental tooth spaces of a patient, and able to extend around a tooth to exert isotropic pressure thereon, the belt having integral locking means fixed thereon for receiving a free end portion of the belt and locking said portion against retraction therefrom and further a means for retaining a fixing member and wherein there are no sharp edges or points on the anchorage.

2. An anchorage as claimed in claim 1, whereby the locking means thereof is attached at one end of the belt and is in the form of a buckle.

3. An anchorage as claimed in claim 2, whereby the plastic buckle provided on the belt thereof faces outwards from the face of the tooth and incorporates a hook and location point for an arch bar.

4. An anchorage as claimed in claim 1, whereby the locking means thereof is in the form of a head having an aperture therethrough or therein for receiving the end portion of the belt.

5. An anchorage as claimed in claim 4, whereby the head of the locking means has a one-way lock mechanism to allow advancement, but resist retraction of the belt in the aperture.

6. An anchorage as claimed in claim 4, whereby the locking head thereof has on its outer face means for retaining a fixing member, for inter-connecting and fixing to other locking heads.

7. An anchorage as claimed in claim 1 having a belt which comprises two sections; a first curved section including the free end of the belt and a second section between the first section and the locking means.

8. An anchorage as claimed in claim 7, whereby the second section of the belt thereof is profiled to co-operate and lockingly engage with the locking head.

9. An anchorage as claimed in claim 7, whereby the first section of the belt thereof has a smooth surface to facilitate passing the belt through inter-dental spaces.

10. An anchorage as claimed in claim 7, whereby the locking means thereof comprises a plurality of inclined teeth on both the second section of the belt and an inner face of the locking head whereby the teeth cooperate such that the belt can only pass through the aperture m one direction.

11. An anchorage as claimed in claim 7, whereby a portion of the belt thereof is made of steel, the first section, having a tensile yield strength of 175 to 2000 $MN/m^2$ and a modulus of elasticity of 175 to 230 $GN/m^2$.

12. An anchorage as claimed in claim 1, whereby the locking means thereof includes an external concave plate to ensure a coherent fitting of the anchorage to a tooth.

13. An anchorage as claimed in claim 1, the belt thereof is 10 to 14 centimeters in length and around 0.6 to 1.0 millimeters in width.

14. An anchorage as claimed in claim 1, the first section of the belt is 1.5 to 3 centimeters long.

15. An anchorage as claimed in claim 1, the locking head is between 7 to 11 millimeters long and between 3 to 5 millimeters in width.

16. An anchorage as claimed in claim 1, whereby the belt thereof is wholly made of plastics material.

17. A method of applying traction using an anchorage comprising a flexible and wholly or substantially plastic belt of a dimension capable of fitting between the intra-dental tooth spaces of a patient, capable of extending around a tooth and exerting isotropic pressure thereon, the belt having an integral locking means fixed thereon for receiving a free end portion of the belt and locking said against retraction therefrom and wherein there are no sharp edges or points on the anchorage, said method comprising the steps of wrapping an elastic band or other suitable means around at least two of said anchorages, such that teeth or fracture points may be drawn to alignment, and holding said teeth or fracture points in place.

* * * * *